(12) United States Patent
Su et al.

(10) Patent No.: US 7,306,818 B2
(45) Date of Patent: Dec. 11, 2007

(54) METHOD FOR PREVENTING AND/OR TREATING VIRAL INFECTION IN AQUATIC ANIMALS

(75) Inventors: Wei-Chih Su, Tainan County (TW); Hsiung Hsiao, Tainan County (TW); Chiung-Hua Yang, Tainan County (TW)

(73) Assignee: ProMd Biotech Co., Ltd., Tainan (TW)

( * ) Notice: Subject to any disclaimer, the term of this patent is extended or adjusted under 35 U.S.C. 154(b) by 204 days.

(21) Appl. No.: 11/026,093

(22) Filed: Jan. 3, 2005

(65) Prior Publication Data

US 2006/0148034 A1 Jul. 6, 2006

(51) Int. Cl.
*A61K 36/00* (2006.01)
*A61K 36/42* (2006.01)
*A01N 65/00* (2006.01)

(52) U.S. Cl. ...................... 424/776; 424/758
(58) Field of Classification Search ............... None
See application file for complete search history.

(56) References Cited

U.S. PATENT DOCUMENTS

| 5,165,925 | A | 11/1992 | Leong |
| 5,401,727 | A | 3/1995 | Rorstad et al. |
| 6,440,466 | B1 | 8/2002 | Desai et al. |
| 6,705,556 | B2 | 3/2004 | Laramore |

OTHER PUBLICATIONS

Direkbusarakom et al., Antiviral Activity of Several Thai Traditional Herb Extracts Against Fish Pathogenic Viruses, Fish Pathology, 1996, vol. 34, No. 4, pp. 209-213.*
Nielsen et al., Ribosome-Inactivating Proteins: A Plant Perspective, Annual Review of Plant Physiology and Plant Molecular Biology, 2001, vol. 52, pp. 785-816.*
Chow et al., Purification, characterization and molecular cloning of trichoanguin, a novel type 1 ribosome-inactivating protein from the seeds of *Trichosanthes anguina*, Biochemical Journal, 1999, vol. 338, pp. 211-219.*
Chang et al., Dietary B-1,3-glucan effectively improves immunity and survival of *Penaeus monodon* challenged with white spot syndrome virus, Fish and Shellfish Immunology, 2003, vol. 15, pp. 297-310.*
Lu et al., Infection competition against grouper nervous necrosis virus by virus-like particles produced in *Escherica coli*, Journal of General Virology, 2003, vol. 84, pp. 1577-1582.*
Yuan et al., Expression of a gene encoding trichosanthin in transgenic rice plants enhances resistance to fungus blast disease, Plant Cell Rep, 2002, vol. 20, pp. 992-998.*
Karunasagar et al., Diagnosis, tereatment and prevention of microbial diseases of fish and shellfish, Current Science, 1999, vol. 76, No. 3, pp. 387-399.*
Chow, Lu-Ping, et al. Purification, characterization and molecular cloning of trichoanguin, a novel type I ribosome-inactivating protein from the seeds of *Trichosanthes anguina*, Biochem. J. (1999) 338, 211-219.

Liu, Wang-Yi and Pu, Zheng, Ribotoxins and Their Applications in Probing the Topographical Structure of Ribosomes, Journal of Natural Toxins, vol. 8, No. 3, (1999).
Gribes, T. Recent Advances in the Uses and Applications of Ribosome-Inactivating Proteins from Plants, Cellular and Molecular Biology, 42 (4), 461-471, (1996).
Maraganore, John M. Purification and Characterization of Trichosanthin—Hormology to the Ricin a Chain and Implications as to Mechanism of Abortifacient Activity, Journal of Biological Chemistry, vol. 262, No. 24, Issue of Aug. 25, 1987, pp. 11628-11633.
Ready, Michael et al. Ricin-like Plant Toxins are Evolutionarily Related to Single-chain Ribosome-inhibiting Proteins from Phytolacca, Journal of Biological Chemistry, vol. 259, No. 24, Issue of Dec. 25, 1984, pp. 15252-15256.
Terenzi, Adelmo et al. Anti-CD30(BER-H2) Immunotoxins Containing the Type-1 Ribosome-Inactivating Proteins Momordin and PAP-S (Pokeweed antiviral Protein from Seeds) Display Powerful Antitumour Activity Against CD30+ Tumour Cells in Vitro and in SCID Mice, British Journal of Haematology, 92, pp. 872-879, (1996).
Bolognesi, Andrea et al. In Vitro Anti-Tumour Activing of Anti-CD80 and Anti-CD86 Immunotoxins Containing Type I Ribosome-Inactivating Proteins, British Journal of Haematology, 110, pp. 351-361 (2000).
Munoz, Raquel et al. Sensitivity of Cancer Cell Lines of the Novel Non-Toxic Type 2 Ribosome-Inactivating Protein Nigrin B, Cancer Letters, 167, pp. 163-169 (2001).
McGrath, Michael S., et al. GLQ223: An Inhibitor of Human Immunodeficiency Virus Replication in Acutely and Chronically Infected Cells of Lymphocyte and Mononuclear Phagocyte Lineage, Proc. Natl. Acad. Sci. USA, vol. 86, pp. 2844-2848, Apr. 1989.
Byers, Vera S., et al. A Phase I/II Study of Trichosanthin Treatment of HIV Disease, AIDS 4, pp. 1189-1196, (1990).
Byers, V.S. et al. A Phase II Study of Effect of Addition of Trichosanthin to Zidovudine in Patients with HIV Disease and Failing Antiretroviral Agents, AIDS Research and Human Retroviruses, vol. 10, No. 4, pp. 413-420, (1994).
Zheng, Y.T. et al. Enhancement of the Anti-Herpectic Effect of Trichosanthin by Acyclovir and Interferon, FEBS Letters, 496, pp. 139-142, (2001).
Gal-On, A. et al. Characterisation of Genetically Modified Cucumber Mosaic Virus Expressing Histidine-Tagged 1a and 2a Proteins, Archives of Virology, 145, pp. 37-50, (2000).
Scholthof, Herman B. et al. Plant Virus Gene Vectors for Transient Expression of Foreign Proteins in Plants, Annu. Rev. of Phytopathol. 34, pp. 299-323, (1996).
Spall, Valerie E. et al. Polyprotein Processing as a Strategy for Gene Expression in RNA Viruses, Seminars in Virology, 8, pp. 15-23, (1997).

\* cited by examiner

*Primary Examiner*—Bruce R. Campell
*Assistant Examiner*—Sharon Hurt
(74) *Attorney, Agent, or Firm*—Akin Gump Strauss Hauer & Feld LLP

(57) ABSTRACT

The present invention provides a preferred method for preventing and/or treating a virus infection in aquatic animals, including the steps of: (i) providing a composition including trichoanguin protein; (ii) adding the composition to an aqueous solution including aquatic animals; and (iii) exposing the aquatic animals to the composition; wherein the composition is added in an amount effective to prevent and/or treat the virus infection. Preferably, the trichoanguin protein is provided by a transgenic plant.

22 Claims, No Drawings

METHOD FOR PREVENTING AND/OR TREATING VIRAL INFECTION IN AQUATIC ANIMALS

BACKGROUND

1. Field of the Invention

The present invention relates generally to a method preventing and/or treating viral infection in aquatic animals. More particularly, the invention provides new uses of trichoanguin protein in preventing and/or treating viral infection in aquatic animals.

2. Background of the Invention

Problem to be solved is that viral diseases to aquaculture is the primary obstacle to the growth of the aquaculture industry. For instance, shrimp culture industry, particularly in Asia, has been threatened by a viral syndrome, commonly known as the "white spot disease," causing heavy mortality and financial losses. Several species of penaeid shrimps viz. *Penaeus monodon, P. japonicus, P. chinensis, P. indicus, P. merguiensis* and *P. setiferus* are known to be infected by this virus. The causative viral agent is known as different names in different countries, such as haematopoietic necrosis baculovirus (HHNBV), systemic ectodermal and mesodermal baculovirus (SEMBV), penaeid rod-shaped DNA virus (PRDV), white spot baculovirus (WSBV), Penaeus monodon non-occluded baculovirusII (PmNOBII), and Penaeus monodon non-occluded baculovirusIII (PmNOBIII). WSSV was found to target various tissues originating from both the mesoderm and ectoderm as evidenced by histopathological studies and in situ hybridization. Furthermore, the virus has also been detected in different organs/tissues including the reproductive organs of wild caught brooders of *P. monodon* indicating its vertical transmission. Besides white spot syndrome virus, there are about 20 shrimp diseases reported to be related to virus, such as infectious hypodermal hematopoietic necrosis virus (IHHNV), baculovirus penaei (BP), baculoviral midgut GI and necrosis virus (BMN), monodon baculovirus (MBV), hepatopan-creatic parvo-like virus (HPV), reo-like virus, Taura syndrome virus (TSV), and yellow head virus (YHV). Such diseases cannot be treated with normal aquiculture drugs.

Nervous necrosis virus (NNV), a pathogen found in many varieties of hatchery-reared marine fish, has caused mass mortality of such fish at their larval or juvenile stages. NNV belongs to the family *Nodaviridae*. Fish nodaviruses isolated from different species (such as SJNNV, BFNNV, JFNNV, TPNNV, RGNNV, GNNV etc.) are closely related to each other owing to the high similarity of the conserved region of their coat protein genes. NNV, also named as fish encephalitis virus (FEV) and piscine neuropathy nodavirus (PNN), is characterized by vacuolation of the nerve tissues. Viral Nervous Necrosis (VNN) disease has been found in many countries under various names such as viral fish encephalitis, fish encephalomyelitis, cardiac myopathy syndrome. The hosts of NNV include many species of marine fish; for example, parrotfish, sea bass, turbot, grouper, stripped jack, tiger puffer, berfin flounder, halibut, barramundi, and spotted wolffish.

Several strategies have been developed to control the viral infection in aquatic animals. U.S. Pat. No. 6,705,556 discloses a composition and method for inducing tolerance and/or immunity to white spot syndrome virus infections including inactivated white spot syndrome virus. U.S. Pat. No. 6,440,466 provides a composition useful as prophylactic and/or therapeutic agent for the management of white spot disease in aquatic animals, said composition containing effective amounts of extracts obtained from the plants, such as Lantena camera, Aegle marmelos, Ocimum sanctum, Mimosa pudica, Cynodon dactylon, Curcuma longa, and Allium sativum, optionally in combination with a pharmaceutically acceptable carrier, diluents or excipients. U.S. Pat. No. 5,401,727 provides a process for stimulating the immune system of the aquatic animals of the class *Osteichthyes* and subphylum *Crustacea* including administering an effective amount of a yeast cell wall glucan composed of glucopyranose units linked by predominately beta-1,3 glycosidic bonds, having at least one branch therefrom of glucopyranose units linked by beta-1,6 glycosidic bonds. U.S. Pat. No. 5,165,925 provides a method for immunizing fish against the infectious pancreatic necrosis virus (IPNV), including administering to susceptible fish a vaccine comprised of an IPNV polypeptide consisting essentially of a polypeptide from the viral A segment and including at least VP2. The polypeptide has been produced in a bacterial host by an expression vector compatible with the host, wherein the expression vector includes an inserted DNA sequence from said A segment of the viral DNA coding for the IPNV polypeptide in the vaccine. Such patents are incorporated herein by reference.

BRIEF SUMMARY OF THE INVENTION

The invention provides a method for preventing and/or treating viral infection in aquatic animals. A ribosome-inactivating protein is provided as an effective agent for preventing and/or treating viral infection in aquatic animals, particularly for preventing and/or treating white spot syndrome virus and nervous necrosis virus infection in aquatic animals.

In accordance with an embodiment of the present invention, there is provided a method for preventing and/or treating a virus infection in aquatic animals, including the steps of:
 (i) providing a composition including trichoanguin protein;
 (ii) adding the composition to an aqueous solution including aquatic animals; and
 (iii) exposing the aquatic animals to the composition; wherein the composition is added in an amount effective to prevent and/or treat the virus infection.

Also in accordance with the present invention, there is provided a method for preventing and/or treating a virus infection in aquatic animals, including the steps of:
 (i) providing a composition including a transgenic plant that expresses trichoanguin protein, or its parts;
 (ii) adding the composition to an aqueous solution including aquatic animals; and
 (iii) exposing the aquatic animals to the composition; wherein the composition is added in an amount effective to prevent and/or treat the virus infection.

Further in accordance with the present invention, there is provided a method for preventing and/or treating white spot syndrome virus infection in shrimps, including the steps of:
 (i) providing a composition including trichoanguin protein;
 (ii) adding the composition to an aqueous solution including shrimps; and
(iii) exposing the shrimps to the composition; wherein the composition is added in an amount effective to prevent and/or treat white spot syndrome virus infection.

Still in accordance with the present invention, there is provided a method for preventing and/or treating white spot syndrome virus infection in shrimps, including the steps of:

(i) providing a composition including a transgenic plant that expresses trichoanguin protein, or its parts;
(ii) adding the composition to an aqueous solution including shrimps; and
(iii) exposing the shrimps to the composition; wherein the composition is added in an amount effective to prevent and/or treat the virus infection.

Yet still in accordance with the present invention, there is provided a method for preventing and/or treating nervous necrosis virus infection in fishes, including the steps of:
(i) providing a composition including trichoanguin protein;
(ii) adding the composition to an aqueous solution including fishes; and
(iii) exposing the fishes to the composition; wherein the composition is added in an amount effective to prevent and/or treat nervous necrosis virus infection.

Further still with the present invention, there is provided a method for preventing and/or treating nervous necrosis virus infection in fishes, including the steps of:
(i) providing a composition including a transgenic plant that expresses trichoanguin protein, or its parts;
(ii) adding the composition to an aqueous solution including fishes; and
(iii) exposing the fishes to the composition; wherein the composition is added in an amount effective to prevent and/or treat the nervous necrosis virus infection.

Additionally further with the present invention, there is provided a feed composition for aquatic animals including a transgenic plant that expresses trichoanguin protein, or its parts.

Additional features and advantages of the present invention will be set forth in part in the description which follows, and in part will be obvious from the description, or may be learned by practice of the invention. The features and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawing, which is incorporated in and constitute a part of this specification, illustrates one embodiment of the present invention and together with the description, serves to explain the principles of the invention.

DETAILED DESCRIPTION OF THE INVENTION

The invention provides a method for preventing and/or treating a virus infection in aquatic animals, including the steps of:
(i) providing a composition including trichoanguin protein;
(ii) adding the composition to an aqueous solution including aquatic animals; and
(iii) exposing the aquatic animals to the composition; wherein the composition is added in an amount effective to prevent and/or treat the virus infection.

The term "trichoanguin (TCA) protein" as used herein refers to a protein having at least about 90% amino acid sequence identity with trichoanguin as reported by Chow, L. P. et al.(Chow, L. P. et al. Purification, characterization and molecular cloning of trichoanguin, a novel type I ribosome-inactivating protein from the seeds of *Trichosanthes anguina. Biochem. J.* 338, 211-219; 1999). Trichoanguin protein has the functional properties of *Trichosanthes anguina*-obtained trichoanguin if it has (a) the ability to inhibit protein synthesis in vitro and/or in vivo (e.g. HeLa cell); and/or (b) N-glycosidase activity. Trichoanguin inhibit protein synthesis by cleaving the N-glycosidic bond of rRNA and preventing the binding of elongation factor 2. The inhibition of protein synthesis leads cytotoxicity. Trichoanguin (TCA) which is a type I ribosome-inactivating protein, was purified from the seeds of the plant *Trichosanthes anguina* (Chow, L. P. et al., 1999).

Ribosome-inactivating proteins (RIPs) are a group of plant enzymes that inhibit protein synthesis in many prokaryotic and eukaryotic cells. RIP is a N-glycosidase that removes a specific adenine base from the highly conserved "S/R domain" on 28S RNA, as far as studied by rendering their 60S ribosomal subunit unable to bind eukaryotic elongation factor 2 (Liu, W. Y. and Pu, Z. Ribotoxins and their applications in probing the topographical structure of ribosomes. *J. Nat. Toxins.* 8, 385-394; 1999). RIPs fall into two main classes, type I and type II RIPs. Type I RIPs are single chain proteins of approximately 24-35 kDa with basic PI values of between 8 and 11. Type II RIPs are dual chain proteins of the form A-B and wherein the B chain possesses a galactose-binding lectin to mediate interaction with cell surface receptors and carbohydrates for protein uptake and receptor-mediated endocytosis (Girbes, T. et al. Recent advances in the uses and applications of ribosome-inactivating proteins from plants. *Cell Mol. Biol.* 42, 461-471; 1996). Several type I RIPs have been purified and characterized from plants, e.g., trichosanthin (TCS) from the root tubers of *Trichosanthes kirilowi* (Maraganore, J. M., Joseph, M. & Bailey, M. C. Purification and characterization of trichosanthin. Homology to the ricin A chain and implications as to mechanism of abortifacient activity. *J. Biol. Chem.* 262, 11628-11633; 1987), pokeweed antiviral protein (PAP) from *Phytolacca Americana* (Ready, M., Wilson, K., Piatak, M. and Robertus, J. D. Ricin-like plant toxins are evolutionarily related to single-chain ribosome-inhibiting proteins from Phytolacca. *J Biol Chem.* 259, 15252-15256; 1984), and □-momorcharin from *Momordia charantia*. The type I RIPs have shown their potential use in the construction of immunotoxins for cancer therapy (Terenzi, A. et al. Anti-CD30 (BER=H2) immunotoxins containing the type-1 ribosome-inactivating proteins momordin and PAP-S (pokeweed antiviral protein from seeds) display powerful antitumour activity against CD30+ tumour cells in vitro and in SCID mice. *Br. J. Haematol.* 92, 872-879; 1996; Bolognesi, A. et al. In vitro anti-tumour activity of anti-CD80 and anti-CD86 immunotoxins containing type 1 ribosome-inactivating proteins. *Br. J. Haematol.* 110, 351-361; 2000; Munoz, R. et al. Sensitivity of cancer cell lines to the novel non-toxic type 2 ribosome-inactivating protein nigrin b. *Cancer Lett.* 167, 163-169; 2001). Besides, TCS is also reported to inhibit the replication of human immunodeficiency virus (HIV) (McGrath, M. S. et al. GLQ223: an inhibitor of human immunodeficiency virus replication in acutely and chronically infected cells of lymphocyte and mononuclear phagocyte lineage. *Proc. Natl. Acad. Sci. U.S.A.* 86, 2844-2848; 1989) and generated great enthusiasm leading to phase I/II clinical trials (Byers, V. S. et al. A phase I/II study of trichosanthin treatment of HIV disease. *AIDS.* 4, 1189-1196; 1990; Byers, V. S. et al. A phase II study of effect of addition of trichosanthin to zidovudine in patients with HIV disease and failing antiretroviral agents. *AIDS Res. Hum. Retroviruses.* 10, 413; 1994). However, side effects precluded further investigation of potential use as a therapeutic agent. A recent study showed that TCS potentiated anti-herpes simplex virus type I (HSV-1) activity when it was used in combination with acyclovir or interferon-□2a (Zheng, Y. T., Chan, W. L., Chan, P., Huang, H. and Tam, S. C. Enhancement of the anti-herpetic effect of trichosanthin by acyclovir and interferon. *FEBS Lett.* 496, 139-142; 2001).

Trichoanguin was found to be a glycoprotein with a molecular weigh of 35 kDa and a pI of 9.114. It consists of 294 amino acids and a comparison of the amino acids sequence of trichoanguin with those of RIPs such as TCS and □-momorcharin reveals 55% and 48% identity, respectively. Molecular homology modeling of trichoanguin indicates that its tertiary structure closely resembles those of TCS and □-momorcharin (Chow, L. P. et al.; 1999). Preferably, the trichoanguin protein is trichoanguin having amino acid sequence identity with trichoanguin as reported by Chow, L. P. et al., 1999.

The term "effective amount" as used herein refers to an amount of a composition which, when administered to an animal, has a desired effect on the animal. For example, an effective amount of a composition for administration to aquatic animals is an amount that prevents and/or treats a virus infection in the animals.

A preferred method of the invention is used for the treatment of viral infection by a virus. The virus can include one or more of white spot syndrome virus, infectious hypodermal hematopoietic necrosis virus, baculovirus penaei, baculoviral midgut GI and necrosis virus, monodon baculovirus, hepatopan-creatic parvo-like virus, reo-like virus, Taura syndrome virus, yellow head virus, infectious pancreatic necrosis virus, Clam virus, grouper Iridovirus, Iridovirus, and European eel Herpesvirus.

Infectious hypodermal hematopoietic necrosis virus (IHHNV), Taura syndrome virus (TSV) and white spot syndrome virus (WSSV) are reported to infect *Litopenaeus vannamei*. Monodon bacul ovirus (MBV) and white spot syndrome virus are reported to infect *Penaeus monodon*. These viruses cause enormous economic loss in aquaculture of shrimps.

Infectious pancreatic necrosis virus (IPNV), a double stranded DNA virus, is a main pathogen in aquaculture of fishes and clamps, especially of *Oreochromis* spp., pike eel (*Muraenesox cinereus*), milkfish (*Chanos chanos*) (also known as giant herring or white mullet), and clam (*Meretrix meretrix*).

Clam virus (CV-TS-1) infects not only clam but also freshwater fishes, which include blue green chromis (also known as blue green damselfishes), Salmon trout (*Oncorhynchus mykiss*), pike eel (*Muraenesox cinereus*), *Cyprinus carpio*, and *Oreochromis* spp.

Grouper Iridovirus (GIV) which is isolated from the lethal cultured grouper in Taiwan infect the kidney and liver of groupers, which include king grouper (*Epinephelus lanceoratus*) and cobias (*Rachycentron canadum*).

Iridovirus, also known as grouper nervous necrosis virus (GNNV) belongs to Betanodavirus genus of Nodaviridae and leads to viral nervous necrosis (VNN) with a very high lethal rate. Japanese sea bass (*Lateolabrax japomcus*), obscure striped puffer (*Fugu obocutus Abe*) and olive flounder (*Paralichthys olivaceus*) are infected by Iridovirus.

European eel Herpesvirus (EEHV) is isolated from European eel. The symptoms of European eel Herpesvirus infection include the accumulations of metabolic inclusion body in the epithelium cells and of melanophage accumulated in the organs.

According to the invention, trichoanguin protein is preferably for treating viral infection in the aquatic animals, including one or more of shrimp, *Oreochromis* spp., pike eel, milkfish, clam, blue green chromis, salmon trout, *Cyprinus carpio*, small abalone, grouper, cobias, Japanese sea bass, Obscure Striped puffer, Olive flounder, European eel, and Stichopus.

The trichoanguin protein according to the invention can be administered orally in a dry or moist form or optionally provided admixed with a feed composition, and wherein preferably is comprised in a feed composition for administration. Additionally, the trichoanguin protein may be administered concurrently with at least one suitable antimicrobial agent and/or at least one suitable vaccine as a single composition.

In one preferred embodiment of the invention, the trichoanguin is provided a transgenic plant. The process for producing trichoanguin protein includes the steps of:

(a) constructing a vector for plant transformation that includes a DNA sequence encoding the trichoanguin protein operably linked to a plant-specific promoter;

(b) transforming a plant cell or tissue with the vector of step (a); and (c) obtaining the trichoanguin protein from the plant cell or tissue of step (b).

According to the invention, the vector for plant transformation includes a DNA sequence encoding the trichoanguin protein operably linked to a plant-specific promoter. In one embodiment of the invention, the vector for plant transformation is based on a conventional vector for plants, e.g., an ordinary binary vector, a cointegration vector or a vector designed to express in plants without T-DNA region. In another embodiment of the invention, the vector for plant transformation is a modified plant virus. Potyviruses are usually utilized for the purpose, and preferably, zucchini yellow mosaic virus (ZYMV) and tobacco mosaic virus (TMV) are suitable according to the invention. In order to transform plants, the trichoanguin protein gene must be inserted into the genome of the plant. Furthermore, the trichoanguin protein gene must contain all the genetic control sequences necessary for the expression of the gene after it has been incorporated into the plant genome. Accordingly, a vector must be constructed to provide the regulatory sequences such that they will be functional upon inserting a desired gene. In one embodiment of the invention, the regulatory sequences include an operably linked plant expressible promoter, a translation initiation codon (ATG) and a plant functional poly(A) addition signal (AATAAA) 3' of its translation termination codon. Additionally, in order to obtain a higher level of expression, untranslated regions 5' and 3' to the inserted genes are provided. When the expression vector/insert construct is assembled, it is used to transform plant cells which are parts of a mature plant or have an ability to regenerate a new plant. These transgenic plants carry the viral gene in the expression vector/insert construct. Once the virus replicates, propagates and spreads, the trichoanguin protein is produced in the plant.

The term "operably linked" as used herein refers to the linking of nucleotide regions encoding specific genetic information such that the nucleotide regions are contiguous, and the functionality of the region is preserved and will perform its function relative to the other regions as part of a functional unit.

Promoters, which are known or found to cause transcription of a foreign gene in plant cells, may be used in the present invention. Such promoters may be obtained from plants or viruses, and for example, the 35S promoter of cauliflower mosaic virus (CaMV) (as used herein, the expression "CaMV 35S" promoter includes variations of CaMV 35S promoter, e.g., promoters derived by means of ligations with operator regions, random or controlled mutagenesis, etc.). Furthermore, the promoters according to the invention can regulate high expression in edible plant parts. In a preferred embodiment of the invention, the vector includes a gene for a selectable marker gene such as an antibiotic-resistance gene (e.g., a kanamycin-resistance gene), a herbicide-resistance gene, a metabolic pathway-related gene, a gene relating to the physical properties, a gene encoding a luciferase (such as GFP), a gene encoding a □-glucuronidase (GUS) or a gene encoding a □-galactosidase, etc. Once the host plant has been selected and the method of gene transfer into the plant has been determined, a constitutive, a developmentally regulated, or a tissue specific promoter for the host plant is selected so that the trichoanguin protein is expressed in the desired part(s) of the plant. Preferably, the vector is ZYMV. The ZYMV-base viral vector permits both systemic spread and efficient, stable expression of foreign proteins. It is considered that the stability may be greatly dependent upon the nucleotide sequence and the length of the insert (Gal-On A, Canto T, Palukaitis P. Characterization of genetically modified Cucumber mosaic virus expressing histidine-tagged 1a and 2a proteins. Arch Virol. 145(1), 37-50; 2000). Zucchini yellow mosaic virus (ZYMV) can replicate and affect quality of cucurbit species such as cucumber, squash, melon, and watermelon. As in all potyviruses, ZYMV can be envisaged as a promising expression vector, since their proteolytic processing strategy of gene expression ensures that a foreign protein synthesized as a part of the viral polyprotein is produced in equimolar amounts with all viral proteins (Scholthof, H. B., Scholthof, K. B. G. and Jackson, A. O. Plant virus gene vectors for transient expression of foreign proteins in plants. Ann. Rev. Phytopathol. 34, 299-323; 1996; Spall, V. E., Shanks, M. and Lomonossoff, G. P. Polyprotein processing as a strategy for gene expression in RNA viruses. Semin. Virol. 8, 15-23; 1997).

In one embodiment of the invention, the trichoanguin protein is incorporated into the ZYMV polyprotein and proteolytically excised as a free form product. The ZYMV-based viral vectors provide the multiple cloning sites and a histidine-tag for the alternative expression of foreign proteins and the convenience for protein purification. The ZYMV TW-TN3 viral vector can well express heterologous proteins between P1 and HC-Pro genes, and this vector construction can stably carry heterologous protein for a long period.

According to the invention, the plants suitable for the invention include any dicotyledonous plants and monocotyledonous plants. In a preferred embodiment, a part or whole plant according to the invention is edible. The plants include, but are not limited in tobacco, potato, zucchini squash, tomato, lettuce, white grape, banana, rice, radish, carrot, apple, soybean, corn, and berries. More preferably, the plants according to the invention include Kennebec variety of potato, *Nicotina benthamiana* and *Cucurbia pepo* L. var. Zucchini.

The choice of the plant cell or tissue for transformation depends on the nature of the host plant and the method for transformation. In one embodiment of the invention, the tissue is regenerable, which retains the ability to regenerate whole, fertile plants following transformation. For example, the plant tissue includes callus, suspension culture cells, protoplasts, leaf segments, stem segments, tassels, pollen, embryos, hypocotyls, tuber segments, meristematic regions, and the like. In another embodiment of the invention, the tissue is a part of a mature plant. Preferably, the tissue is edible or has an ability to express and/or purifying enormously the trichoanguin proteins according to the invention. For example, the tissue includes leaves, fruits, stems, tubers, and the like.

According to the invention, the step of transforming the plant cell or tissue with the vector includes (1) Agrobacterium-mediated gene transferring; (2) direct DNA uptaking; or (3) plant virus infecting.

The Agrobacterium system is especially viable in the creation of transgenic dicotyledenous plants. In the preferred embodiment of the present invention, the Agrobacterium-Ti plasmid system is utilized. The tumor-inducing (Ti) plasmids of *A. tumefaciens* contain a transforming DNA (T-DNA) which is transferred to plant cells and then integrates into the plant host genome with the help of inducible virulence (vir) genes of Agrobacterium. The vector including the trichoanguin protein gene, T-DNA region and a selectable marker gene can be constructed in *Escherichia coli* and then transferred into Agrobacterium via a conjugation mating or direct uptaking by Agrobacterium. Those skilled in the art should recognize that there are many Agrobacterium strains, such as *A. tumefaciens* and *A. rhizogenes*, and plasmid constructions that can be used to optimize genetic transformation of plants. According to the invention, those skilled in the art can choose the method for inoculation depending upon the plant species and the Aarobacterium delivery system; for example, leaf disc procedure or in vitro transformation of regenerating protoplasts.

According to the invention, a direct physical method of introducing foreign DNA into the plant cells can also applied. In electroporation, the protoplasts are briefly exposed to a strong electric field. In microinjection, the DNA is mechanically injected directly into the cells using micropipettes. In microparticle bombardment, the DNA is adsorbed on microprojectiles such as magnesium sulfate crystals or tungsten particles. A direct incubation of DNA with germinating pollen is also included.

According to the invention, when using the modified plant viruses as vectors, the viruses can be utilized to infect plants at wound sites. Optionally, the process according to the invention further includes a step of regenerating a transgenic plant from the plant cell or tissue before step (c). The plant cell or tissue transformed is then regenerated to form a transgenic plant. As used herein, the term "regeneration" refers to growing a whole plant from a plant cell, a group of plant cells or a plant part. The methods for plant regeneration are well known to those skilled in the art. When transformation is of an organ part, regeneration can be from the plant callus, explants, organs or parts. Such methods for regeneration are also known to those skilled in the art.

There are several strategies for obtaining the trichoanguin protein from plant cells or whole plants. In one embodiment, the method of obtaining the trichoanguin protein according to the invention is accomplished by obtaining the plant cell or whole plant or portions thereof such as fruits, leaves, stems, and tubers or extract thereof. In another embodiment, the trichoanguin protein is provided by further purifying the trichoanguin protein from the extract. In still another embodiment, the trichoanguin protein is obtained by merely harvesting at least a part of a transgenic plant, such as fruit or seeds. In still another embodiment, the trichoanguin protein is provided in the form of the transgenic plant itself.

The present invention also provides a method for preventing and/or treating a virus infection in aquatic animals, including the steps of:

(i) providing a composition including a transgenic plant that expresses trichoanguin protein, or its parts;

(ii) adding the composition to an aqueous solution including aquatic animals; and
(iii) exposing the aquatic animals to the composition; wherein the composition is added in an amount effective to prevent and/or treat the virus infection.

The present invention also relates to a method for preventing and/or treating white spot syndrome virus infection in shrimps, including the steps of:
(i) providing a composition including trichoanguin protein;
(ii) adding the composition to an aqueous solution including shrimps; and
(iii) exposing the shrimps to the composition; wherein the composition is added in an amount effective to prevent and/or treat white spot syndrome virus infection.

Furthermore, the invention provides a method for preventing and/or treating white spot syndrome virus infection in shrimps, including the steps of:
(i) providing a composition including a transgenic plant that expresses trichoanguin protein, or its parts;
(ii) adding the composition to an aqueous solution including shrimps; and
(iii) exposing the shrimps to the composition; wherein the composition is added in an amount effective to prevent and/or treat the virus infection.

The invention provides a method for preventing and/or treating nervous necrosis virus infection in fishes, including the steps of:
(i) providing a composition including trichoanguin protein;
(ii) adding the composition to an aqueous solution including fishes; and
(iii) exposing the fishes to the composition; wherein the composition is added in an amount effective to prevent and/or treat nervous necrosis virus infection.

Furthermore, the invention provides a method for preventing and/or treating nervous necrosis virus infection in fishes, including the steps of:
(i) providing a composition including a transgenic plant that expresses trichoanguin protein, or its parts;
(ii) adding the composition to an aqueous solution including fishes; and
(iii) exposing the fishes to the composition; wherein the composition is added in an amount effective to prevent and/or treat the nervous necrosis virus infection.

The present invention also provides a feed composition for aquatic animals including a transgenic plant that expresses trichoanguin protein, or its parts. Furthermore, the invention provides a feed composition for aquatic animals including trichoanguin protein.

The following Examples are given for the purpose of illustration only and are not intended to limit the scope of the present invention.

EXAMPLE 1

Expression Trichoanguin Protein in A Transgenic P1

Construction of ZYMV-trichoanguin recombinant plant virus: The trichoanguin (TCA) gene flanked with restriction enzyme cutting sites Sph I and Kpn I was amplified with the primer set (5'-GCA TGC GCA CTC TCC TTT TTC TTT CTC G-3', SEQ ID No. 1 and 5'-GGT ACC CAT TGT AAC ATA ATT TCC-3' SEQ ID No. 2) from the cDNA template. The PCR was performed with the first cycle at 94° C. for 1 min, following by 33 cycles at 94° C. for 30 sec, 2 min at 55° C., and 2 min at 72° C.; and the final cycle for 5 min at 72° C. in a GeneAmp™ thermocycler (Perkin-Elmer® Applied Biosystems, Foster City., Calif.). The 0.9 kb PCR products were eluted from agarose gel and ligated into TOPO TA vector pCR2.1 (Invitrogen®, Carlsbad, Calif.). The sequence of cloned TCA gene was confirmed by ABI automatic sequencer (Perkin-Elmer® Applied Biosystems, Foster City., Calif.). The TCA gene in the pCR2.1 was treated with two restriction enzymes, Sph I/Kpn I, and the 0.9 kb fragment of TCA gene was cloned into the viral vector p35SZYMVGFPhis-420 in the same restriction enzyme sites.

Plant inoculation: Systemic host *Cucurbita pepo* L. var. Zucchini at the two cotyledons stage and local lesion host *Chenopodium quinoa* Willd. with four fully expanded leaves were used for infectivity assays. The plasmids (1 □g) were used to infect *C. quinoa* plants by mechanical inoculation. At 7 days post inoculation (dpi), single lesions were isolated and mechanically transferred to plants of the systemic host zucchini squash. All plants inoculated were kept in a temperature-controlled greenhouse (23-28° C.) for observation.

Stability test: The leaved of Zucchini squash with typical ZYMV-induced symptoms was taken for the stability assay. And the non-infected Zucchini squash leaves were used as negative control. The infected leaves were mixed with Kpi buffer in the ration of 1 to 4 and homogenized on ice. The mixture was centrifuged twice at 3000 g for 15 minutes and 30000 g for 30 minutes respectively. Then, the supernatant was collected and put into 1.5 ml eppendroff. The samples were storaged at −20° C., 4° C., 25° C. and 37° C. respectively. The ELISA assay was performed at $1^{st}$, $3^{rd}$, $7^{th}$, $21^{st}$, $30^{th}$ and $90^{th}$ days.

Each well of 96 well plate contained 40 □L sample solution and 160 □L of coating buffer and incubated at 37° C. After one hour, discard the solution and wash the plate 3 times with wash buffer. After drying the plate by flapping on a towel, the anti-TCA serum was added in each well and the plate was incubated at 37° C. for 1 hour, then, the anti-mouse-IgG was added for analysis. After incubated at 37° C. for 1 hour, the phosphatase substrate was added and the photoemission was detected at wavelength of 405 nm by photometer 2 hours later to confirm the expression of TCA protein. If the $OD_{405}$ value of infected plant reaches twice higher than healthy plant, the over expression of TCA can be sured. Each sample was performed in duplex.

The result is shown in Table 1. The OD value of ZYMV-trichoanguin is more than 2 times of that of SH-15. Given the above, trichoanguin was successfully expressed in the transgenic plant.

TABLE 1

| | ZYMV-Trichoanguin | SH-15[1] |
|---|---|---|
| Control[2] | 0.249 | 0.154 |
| | 0.257 | 0.150 |
| Plant 1 | 3.566 | 0.257 |
| | 3.593 | 0.260 |
| Plant 2 | 3.475 | 0.335 |
| | 3.435 | 0.342 |
| Plant 3 | 3.593 | 0.394 |
| | 3.496 | 0.454 |

[1]SH-15 is a protein expressed in a normal Zucchini squash. The detection of SH-15 was conducted with SH-15 antibody.
[2]The value of ZYMV-Trichoanguin was detected with ZYMV antibody.

The ZYMV OD values of the ZYMV-inoculated plant range from 3.4 to 3.5 while those of the control plant are about 0.25. In addition, the SH-15 expression of the ZYMV-inoculated plant is also higher than that of the control plant. Furthermore, the Western blot analysis was also conducted with anti-TCA serum.

EXAMPLE 2

Low Dosage of Trichoanguin for Preventing and/or Treating Viral Infection in Shrimp Trichoanguin preparation: The leaves of the plant that expresses trichoanguin in Example 1 were mixed with 10 mM KPI buffer (containing $K_2HPO_4$ and $KH_2PO_4$) in the ratio of 1:4 and homogenized at 4° C.

Animal: The shrimps (*Penaeus monodom*) weighting 4.94 g in average were fed with the density of 20 shrimps/m² and the salinity of 3.5% at 28-30° C. The feed composition was added with 0, 2, 20, 200% of the homogenized solution and the dosage was 3% of the total shrimp weight. After 5 days, the shrimps were challenged by feeding with white spot syndrome virus infected shrimp bodies. The survival rate after 7 days were listed in Table 2. Each group was conducted in triplicate.

TABLE 2

| | TCA concentration (%) | | | |
|---|---|---|---|---|
| | 0 | 2 | 20 | 200 |
| Survival rate (%) | 14 ± 6 | 13 ± 7 | 19 ± 11 | 22 ± 2 |

Many shrimps died on day 3 after challenge and thereafter. The highest survival rate is that of the group treating with 200% TCA. However, the differences between the groups are not significant in statistics.

EXAMPLE 3

High Dosage of Trichoanguin for Preventing and/or Treating Viral Infection in Shrimp Trichoanguin preparation: The leaves of the plant that expresses trichoanguin in Example 1 were mixed with 10 mM KPI buffer (containing $K_2HPO_4$ and $KH_2PO_4$) in the ratio of 1:4 and homogenized at 4° C. The homogenized solution was concentrated in 20 folds by freeze drying.

Animal: The shrimps (*Penaeus monodom*) weighting 5.04 g in average were fed with the density of 20 shrimps/m² and the salinity of 3.5% at 20-24° C. The feed composition was added with 0, 2, 40, 60% of the 20-fold concentrated homogenized solution and the dosage was 3% of the total shrimp weight. After 5 days, the shrimps were challenged by feeding with White Spot Syndrome Virus infected shrimp bodies. The survival rate after 7 days were listed in Table 3. Each group was conducted in duplicate.

TABLE 3

| | TCA concentration (%) | | | |
|---|---|---|---|---|
| | 0 | 2 | 40 | 60 |
| Survival rate (%) | 0 | 50 ± 20 | 85 ± 15 | 85 ± 15 |

Many shrimps died on day 5 after challenge and thereafter. All shrimps of the control group (without treatment) died on day 7 after challenge. The survival rates of the groups treated with 40% and 60% trichoanguin is about 85% and that of the group treated with 20% trichoanguin is about 50%. It shows that the high dosage of trichoanguin effects on preventing/treating white spot syndrome virus infection.

EXAMPLE 4

Trichoanguin for Preventing and/or Treating Viral Infection in Fish

Trichoanguin preparation: The leaves of the plant that expresses trichoanguin in Example 1 were mixed with 10 mM KPI buffer (containing $K_2HPO_4$ and $KH_2PO_4$) in the ratio of 1:4 and homogenized at 4° C.

Animal: The groupers (*Epinephelus lanceolatus*) weighting 6.2 g in average were fed with the salinity of 3.5% at 28-31° C. Every thirteen fishes was fed in a 90-L pond. The feed composition was added with 0, 0.2, 1.0, 2.0, and 4.0% of the homogenized solution and freeze dried. The dosage was 5% of the total fish weight. After 5 days, the shrimps were challenged by feeding with nervous necrosis virus infected fish bodies. The survival rate after 14 days were listed in Table 4. Each group was conducted in duplicate.

TABLE 4

| Day after challenge | TCA concentration (%) | | | | |
|---|---|---|---|---|---|
| | 0 | 0.2 | 1.0 | 2.0 | 4.0 |
| 2 | 100 | 94.9 ± 8.9 | 97.4 ± 4.4 | 100 | 100 |
| 3 | 71.8 ± 24.7 | 76.9 ± 20.4 | 84.6 ± 20.4 | 87.2 ± 11.8 | 100 |
| 4 | 10.3 ± 11.2 | 38.5 ± 7.7 | 66.7 ± 32.0 | 79.5 ± 19.4 | 100 |
| 5 | 0 | 20.5 ± 19.4 | 38.5 ± 15.4 | 66.7 ± 31.1 | 100 |
| 6 | — | 0 | 17.9 ± 16.0 | 38.5 ± 7.7 | 100 |
| 9 | — | — | 7.7 ± 13.3 | 20.5 ± 11.8 | 100 |
| 7 | — | — | 0 | 12.8 ± 11.8 | 66.7 ± 4.4 |
| 8 | — | — | — | 2.6 ± 4.4 | 59.0 ± 4.4 |
| 9 | — | — | — | 0 | 53.8 ± 7.7 |
| 10 | — | — | — | — | 51.3 ± 11.8 |
| 11 | — | — | — | — | 38.5 ± 15.4 |
| 12 | — | — | — | — | 30.8 ± 27.7 |
| 13 | — | — | — | — | 0 |

Many fishes died on day 3 after challenge and thereafter. All fishes of the control group (without treatment) died on day 5 after challenge. However, the fishes of the group treated with 4% trichoanguin died on day 8 after challenge and thereafter. It shows that trichoanguin effects on preventing/treating nervous necrosis virus infection.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A method for inhibiting white spot syndrome virus infection in shrimps, comprising:
   (i) providing a composition comprising trichoanguin protein;
   (ii) adding the composition to an aqueous solution comprising shrimps; and
   (iii) exposing the shrimps to the composition,
   wherein the composition is added in an amount effective to inhibit white spot syndrome virus infection.

2. The method of claim 1, wherein the composition is a feed composition.

3. The method of claim 1, wherein the trichoanguin protein is provided by a transgenic plant.

4. The method of claim 3, wherein at least one portion of the transgenic plant is edible.

5. The method of claim 3, wherein the transgenic plant is selected from the group consisting of tobacco, potato, zucchini squash, tomato, lettuce, white grape, banana, rice, radish, carrot, apple, soybean, corn, and berries.

6. The method of claim 3, wherein the trichoanguin protein is provided in the form of the transgenic plant itself, a part of the plant, fruit, leaves, stems, tubers, seed or extract thereof.

7. A method for inhibiting white spot syndrome virus infection in shrimps, comprising:
   (i) providing a composition comprising a transgenic plant that expresses trichoanguin protein, or a part of the transgenic plant that expresses trichoanguin protein;
   (ii) adding the composition to an aqueous solution comprising shrimps; and
   (iii) exposing the shrimps to the composition,
   wherein the composition is added in an amount effective to prevent and/or treat inhibit the virus infection.

8. The method of claim 7, wherein the composition is a feed composition.

9. The method of claim 7, wherein at least one portion of the transgenic plant is edible.

10. The method of claim 7, wherein the transgenic plant is selected from the group consisting of tobacco, potato, zucchini squash, tomato, lettuce, white grape, banana, rice, radish, carrot, apple, soybean, corn, and berries.

11. The method of claim 7, wherein the trichoanguin protein is provided in the form of the transgenic plant itself, a part of the plant, fruit, leaves, stems, tubers, seed or extract thereof.

12. A method for inhibiting nervous necrosis virus infection in fishes, comprising:
    (i) providing a composition comprising trichoanguin protein;
    (ii) adding the composition to an aqueous solution comprising fishes; and
    (iii) exposing the fishes to the composition,
    wherein the composition is added in an amount effective to prevent and/or treat inhibit nervous necrosis virus infection.

13. The method of claim 12, wherein the composition is a feed composition.

14. The method of claim 12, wherein the trichoanguin protein is provided by a transgenic plant.

15. The method of claim 14, wherein at least one portion of the transgenic plant is edible.

16. The method of claim 14, wherein the transgenic plant is selected from the group consisting of tobacco, potato, zucchini squash, tomato, lettuce, white grape, banana, rice, radish, carrot, apple, soybean, corn, and berries.

17. The method of claim 14, wherein the trichoanguin protein is provided in the form of the transgenic plant itself, a part of the plant, fruit, leaves, stems, tubers, seed or extract thereof.

18. A method for inhibiting nervous necrosis virus infection in fishes, comprising:
    (i) providing a composition comprising a transgenic plant that expresses trichoanguin protein, or its-parts a part of the transgenic plant that expresses trichoanguin protein;
    (ii) adding the composition to an aqueous solution comprising fishes; and
    (iii) exposing the fishes to the composition,
    wherein the composition is added in an amount effective to inhibit the nervous necrosis virus infection.

19. The method of claim 18, wherein the composition is a feed composition.

20. The method of claim 18, wherein at least one portion of the transgenic plant is edible.

21. The method of claim 18, wherein the transgenic plant is selected from the group consisting of tobacco, potato, zucchini squash, tomato, lettuce, white grape, banana, rice, radish, carrot, apple, soybean, corn, and berries.

22. The method of claim 18, wherein the trichoanguin protein is provided in the form of the transgenic plant itself, a part of the plant, fruit, leaves, stems, tubers, seed or extract thereof.

* * * * *